(12) United States Patent
Yamin et al.

(10) Patent No.: US 8,889,715 B2
(45) Date of Patent: Nov. 18, 2014

(54) SUBSTITUTED PYRIDOXINE-LACTAM CARBOXYLATE SALTS

(71) Applicant: Alcobra Ltd., Tel Aviv-Yafo (IL)

(72) Inventors: Rina Yamin, Rehovot (IL); Dalia Megiddo, Nataf (IL)

(73) Assignee: Alcobra Ltd., Tel Aviv (IL)

( * ) Notice: Subject to any disclaimer, the term of this patent is extended or adjusted under 35 U.S.C. 154(b) by 0 days.

(21) Appl. No.: 13/667,198

(22) Filed: Nov. 2, 2012

(65) Prior Publication Data

US 2013/0059887 A1   Mar. 7, 2013

Related U.S. Application Data

(63) Continuation of application No. 13/056,943, filed as application No. PCT/IL2009/000741 on Jul. 29, 2009, now abandoned.

(60) Provisional application No. 61/084,514, filed on Jul. 29, 2008.

(51) Int. Cl.
| | |
|---|---|
| *C07D 401/12* | (2006.01) |
| *A61K 31/4439* | (2006.01) |
| *A61K 31/4545* | (2006.01) |
| *C07D 213/67* | (2006.01) |
| *A61P 25/32* | (2006.01) |
| *A61P 9/00* | (2006.01) |
| *A61P 9/12* | (2006.01) |
| *A61P 9/10* | (2006.01) |
| *A61P 1/00* | (2006.01) |
| *A61P 1/18* | (2006.01) |
| *A61P 1/16* | (2006.01) |
| *A61P 35/00* | (2006.01) |
| *A61P 3/00* | (2006.01) |
| *A61P 25/00* | (2006.01) |

(52) U.S. Cl.
CPC .................................. *C07D 213/67* (2013.01)
USPC ......... 514/318; 546/278.4; 546/193; 514/343

(58) Field of Classification Search
CPC .. C07D 207/16; C07D 201/14; C07D 211/60; C07D 213/02; A61K 2300/00; A61K 31/401; A61K 31/4015; A61K 31/4415; A61K 31/4425; A61K 31/452
See application file for complete search history.

(56) References Cited

U.S. PATENT DOCUMENTS

| | | | |
|---|---|---|---|
| 4,313,952 A | 2/1982 | Baldacci | |
| 6,541,043 B2 | 4/2003 | Lang | |
| 2002/0192303 A1 | 12/2002 | Arver et al. | |
| 2003/0147957 A1 | 8/2003 | Licht et al. | |
| 2003/0148992 A1 | 8/2003 | Block et al. | |
| 2004/0162270 A1 | 8/2004 | Oslick et al. | |
| 2005/0043290 A1* | 2/2005 | Cumming et al. | 514/210.2 |
| 2005/0271739 A1 | 12/2005 | Wang | |
| 2007/0248696 A1 | 10/2007 | Maletto et al. | |
| 2008/0146577 A1 | 6/2008 | Matalon et al. | |
| 2009/0081179 A1 | 3/2009 | Kiliaan et al. | |
| 2010/0256198 A1 | 10/2010 | Megiddo et al. | |
| 2012/0264781 A1 | 10/2012 | Yamin et al. | |
| 2012/0277270 A1 | 11/2012 | Megiddo et al. | |
| 2013/0012549 A1 | 1/2013 | Yamin et al. | |

FOREIGN PATENT DOCUMENTS

| | | |
|---|---|---|
| CN | 1650862 A | 8/2005 |
| EP | 511943 A2 | 11/1992 |
| FR | 2172906 | 10/1973 |
| GB | 1286161 A | 8/1972 |
| WO | WO-9418965 A1 | 9/1994 |
| WO | WO-03003981 A2 | 1/2003 |
| WO | WO-2005048974 A2 | 6/2005 |
| WO | WO-2008/066353 | 6/2008 |
| WO | WO-2009/004629 | 1/2009 |
| WO | WO-2010013242 A1 | 2/2010 |
| WO | WO-2010150261 A1 | 12/2010 |

OTHER PUBLICATIONS

Ikawa, M. Archives of Biochemistry and Biophysics 1967, 118, 497-500.*
"'Metadoxil' Drug Information." *ABCJ.* Jul. 7, 1997. (Russian Original and English Translation).
"Alcohol Dependence." Guidance for Medicine: Diagnostics and Therapy, *The Merck Manual.* 2(1997):15. (Russian Original and English Translation).
"Efficacy Study of Metadoxine SR Formulation in Attention Deficit Hyperactivity Disorder (ADHD) Subjects (NCT00995085)." Clinicaltrials.gov (Oct. 2009).
"Prolongation Substances (Prolongators)." *Technology of Drug Forms.* Moscow, Russia: Meditsina Publishers. Kondratieva, ed. vol. 1, Par. 5.3.4.(1991):106-108. (Russian Original and English Translation).
"Results." *Drug Preparations by Medical Scientific Manufacture Complex Biotica,* Moscow (2002):17, 19, 20, 22, 24. Russian Original and English Translation).
"Vitamin B6." *Alveda Pharma.* 2001. Web. Feb. 2, 2005. http://www.alvedapharma.com/PDF/PyridoxineEnglish.pdf.
Addolorato et al. "Metadoxine in the Treatment of Acute nd Chronic Alcoholism: A Review." *Int. J. Immunopath. Pharmacol.* 16.3(2003):207-214.

(Continued)

*Primary Examiner* — Samantha Shterengarts
*Assistant Examiner* — Amanda L Aguirre
(74) *Attorney, Agent, or Firm* — Cooley LLP

(57) ABSTRACT

The present invention provides salt adducts comprising at least one positively charged moiety being a pyridoxine or a derivative thereof and at least one carboxylated 5- to 7-membered lactam ring, optionally additionally substituted, methods of their preparation, and pharmaceutical compositions and medicaments comprising them. Salt adducts of the invention and compositions comprising them may be used to in the treatment of diseases or disorders associated with or inflicted by alcohol consumption.

14 Claims, No Drawings

(56) References Cited

OTHER PUBLICATIONS

Ajay et al. "Design, Development and In Vitro Evaluation of Metdoxine Microbeads: Ionic Gelation Method." *Pharma. Res.* 5.1(2011):62-69.

Annoni et al. "Pyridoxol L,2-Pyrrolidon-5 Carboxylate Prevents Active Fibroplasia in CCl4-Treated Rats." *Pharm. Res.* 25.1(1992):87-93.

Antonelli et al. "Pyroglutamic Acid Administration Modifies the Electrocorticogram and Increases the Release of Acetycholine and Gaba From the Guinea-Pig Cerebral Cortex." *Pharmacol. Res. Commun.* 16.2(1984):189-197.

Aungst. "Intestinal Permeation Enhancers." *J. Pharm. Sci.* 89(2000):429-442.

*Biotics.* (2002):18. (Russian Original and English Translation).

Christie. "Scotland's Drinking Laws Set for Reform to Stem Alcohol Problems." *BMJ.* 327.7413(2003):467.

Elia et al. "Treatment of Attention-Deficit-Hyperactivity Disorder." *N. Engl. J. Med.* 340.10(1999):780-788.

Felicioli et al. "Effects of Pyridoxine-Pyrrolidon-Carboxylate on Hepatic and Cerebral ATP Levels in Ethanol Treated Rats." *Int. J. Clin. Pharmacol. Ther. Toxicol.* 18.6(1980):277-280. (Abstract Only).

Guerrini et al. "A Follow Up Study on the Efficacy of Metadoxine in the Treatment of Alcohol Dependence." *Substance, Abuse Treatment, Prevention and Policy.* 1(2006):35.

Johansson et al. "Studies on the Metabolism of Labeled Pyridoxine in Man." *Am. J. Clin. Nutr.* 18(1966):185-196.

Lalazar et al. "A Novel Slow Release Formulation of Metadoxine Improves Motor and Cognitive Function, Decreases Craving After Alcohol Ingestion in Healthy Volunteers: Results of a Phase I Clinical Trial." *Hepatol.* 50.4(2009):611A. (Abstract #650).

Langer. "New Methods of Drug Delivery." *Science.* 249. 4976(1990):1527-1533.

Lingetti et al. "Treatment of Cerebral Vasculopathies With Metadoxine." *Acta Gerontol.* 30.3(1980):230-234. (English Translation).

Morse et al. "The Definition of Alcoholism." *JAMA.* 268. 8(2008):1012-1014.

Pal'tsev et al. "Non-Alcoholic Fatty Liver Disease: Age Peculiarities, Breakthrough in Pathogenic Therapy." *Eksp. Klin. Gastroenterol.* 8(2009):19-25. (English Abstract Only).

Pellegrini-Giampietro et al. "Pyrrolidone Carboxylic Acid in Acute and Chronic Alcoholism." *Recenti Progressi Medicina.* 80.3(1989):160-164.

Safonova et al. "Metadoxil in the Treatment of Hepatotoxic Action of Cytostatics." *Issues Oncol.* 5(2005):599-600. (Russian Original and English Abstract).

Sinforiani et al. "Effects of Metadoxine (Metadoxil®) on the Early Phase of Cognitive Recovery in Abstinent Alcoholics." *Clin. Trial. J.* 27.2(1990):103-111.

Vonghia et al. "Acute Alcohol Intoxication." *Eur. J. Int. Med.* 19.8(2008):561-567.

Yifan et al. "Influence of Metadoxine on the Concentration of Ethanol in Blood of Rats With Acute Ethanol Intoxication." *J. Health Toxicol.* 17.2(2003). (English Translation of Summary).

International Search Report of PCT/IL2009/000741 Dated Nov. 10, 2009 With Written Opinion of the ISA.

Lu et al., "Pharmacokinetics of Metadoxine for Injection After Repeated Doses in Healthy Volunteers," Chin. Med. J. 2007, 120(2), 155-168.

Shpilenya et al., "Metadoxine in Acute Alcohol Intoxication: A Double-Blind, Randomized, Placebo-Controlled Study," Clin. Exp. Res. 2002, 26(3), 340-346.

Guidance for Industry, Estimating the Maximum SFE Starting Dose in Initial Clinical Trials for Therapeutics in Adult Healthy Volunteers, Food and Drug Administration (FDA) and Center for Drug Evaluation and Research (CDER), Jul. 2005.

Calabrese, V. et al., "Effecs of Metadoxine on Cellular Formation of Fatty and Ethyl Esters in Ethanol Treated Rats," Int. J. Reac. XVII(3), 101-108, 1995.

Gutierrez-Ruiz, M.C. et al., "Metadoxine Prvents Damage Produced by Ethanol and Acetaldehyde in Hepatocyte and Hepatic Stellate Cells in Culture," Pharmacological Research, 44(3), 2001.

\* cited by examiner

SUBSTITUTED PYRIDOXINE-LACTAM CARBOXYLATE SALTS

CROSS-REFERENCE TO RELATED APPLICATION

The present application is a continuation of application Ser. No. 13/056,943, filed Jan. 31, 2011, which was a National Stage of International Application No. PCT/IL2009/000741, filed Jul. 29, 2009, designating the United States and claiming priority from U.S. Provisional Patent Application No. 61/084,514, filed on Jul. 29, 2008. The foregoing applications are incorporated herein by reference in their entirety.

TECHNICAL FIELD

The present invention relates to salt adducts comprising at least one pyridoxine or a derivative thereof and at least one carboxylated 5- to 7-membered lactam ring and uses thereof.

BACKGROUND OF THE INVENTION

Alcohol-induced liver diseases are a common disorder in modern communities and societies. For example, in Europe there are more than 45 million individuals showing signs of alcohol-related damage such as liver disease and myopathies. Chronic alcohol consumption increases hepatic accumulation of triglycerides and leads to hepatic steatosis, which is the earliest and most common response to severe alcohol intoxication.

Thus, severe alcohol intoxication is a serious disease that should be treated with medication in order to reduce the damage to the human body of the alcohol intoxicated individual. For example, alcohol intoxication can be treated with metadoxine (pyridoxine L-2-pyrrolidone-5-carboxylate). Metadoxine is a salt of the corresponding anion of L-2-pyrrolidone-5-carboxylic acid (L-2-pyroglutamic acid) (1) and the protonated derivative of pyridoxine (vitamin B6) (2), having the following structures:

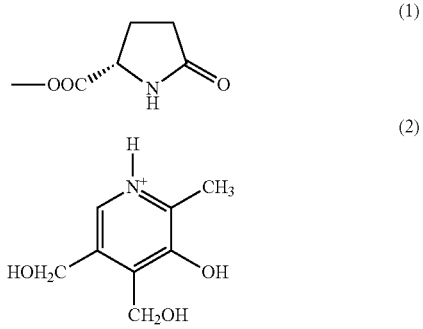

WO 2008/066353 discloses the use of Metadoxine in the treatment of alcohol intoxication either alone or in combination with other active agents. WO 2008/066353 mentions that metadoxine does not inhibit the expression and activation of an alcohol-induced cytochrome P450 2E1, which is the key enzyme involved in alcohol-induced toxicity. Thus, the use of metadoxine may be limited.

Several studies have shown that in order to effectively treat alcohol intoxication, there is a need for a relatively high daily dose (ca. 900 mg) administered intravenously (see, e.g., Lu et al. *Chin. Med. J.* 2007, 120 (2), 155-168 and Shpilenya et al. *Alcohol Clin. Exp. Res.* 2002, 26 (3), 340-346). These studies disclose side effects associated with the use of metadoxine, including nausea and vomiting.

Thus, there exists a need in the art for effective and safe drugs for treating alcohol intoxication and other associated diseases.

SUMMARY OF THE INVENTION

The present invention provides, inter alia, salt adducts comprising at least one pyridoxine or a derivative thereof and at least one carboxylated 5- to 7-membered lactam ring, methods of their preparation, medicaments comprising those compounds, therapeutic treatments utilizing salt adducts of the invention and uses thereof in the preparation of pharmaceutical compositions.

In one aspect, the invention provides a salt adduct comprising at least one positively charged moiety being a pyridoxine or a derivative thereof and at least one carboxylated 5- to 7-membered lactam ring, optionally additionally substituted; provided that when said carboxylated lactam ring is an L-2-pyroglutamate (compound (1)), said positively charged moiety is other than pyridoxine (compound (2)).

In another aspect, the invention provides a pharmaceutical composition comprising a salt adduct of the invention.

In further aspect, the invention provides a use of a salt adduct of the disclosure for the preparation of a pharmaceutical composition for the treatment or prevention of a disease or disorder associated with or inflicted by alcohol consumption.

The invention also provides a use of a salt adduct of the invention for the preparation of a pharmaceutical composition capable of shortening the half-life of ethanol in the blood of a subject.

In another aspect, the invention provides a method for treating or preventing a disease or disorder associated with or inflicted by alcohol consumption, comprising administering to a subject in need thereof an effective amount of a salt adduct of the invention.

In a further aspect, the invention provides methods of shortening the half-life of ethanol in the blood of a subject, comprising administering to a subject in need thereof an effective amount of a salt adduct of the invention.

In another aspect, the invention provides a kit for reducing the effect of alcohol intoxication, comprising at least one container comprising a salt adduct of the invention, and instructions for use thereof.

DETAILED DESCRIPTION OF THE INVENTION

In one aspect, the present invention provides a salt adduct comprising at least one positively charged moiety being a pyridoxine or a derivative thereof and at least one carboxylated 5- to 7-membered lactam ring, optionally additionally substituted; provided that when said carboxylated lactam ring is an L-2-pyroglutamate (compound (1)), said positively charged moiety is other than pyridoxine (compound (2)).

As used herein the term "salt adduct" is meant to encompass a salt product of a direct addition of two or more distinct ions, wherein the overall charge of the salt adduct is zero. In certain embodiments, the salt adduct comprises one positively charged moiety having a single positive charge functional group (i.e., the positively charged moiety is charged with +1 net charge) and one negatively charged moiety having a single negative charge functional group (i.e., the negatively charged moiety is charged with −1 net charge). In certain embodiments, the salt adduct comprises one positively charged moiety having two positively charged functional groups, which may be the same or different (i.e., the positively charged moiety is charged with +2 net charge) and two negatively charged moieties, which may be the same or different, and each having a single negative charged functional group (i.e., each negatively charged moiety is charged with −1 net charge). In certain embodiments, the salt adduct comprises two positively charged moieties, which may be the same or different, having each one positively charged functional group (i.e., each positively charged moiety is charged with +1 net charge) and one negatively charged moiety, having two negatively charged functional groups, being the same or different (i.e., the negatively charged moiety is charged with −2 net charge). In certain embodiments, the salt adduct comprises a positively charged moiety charged with +n net charge (originating from one or more positively charged functional groups, which may be the same or different), and a negatively charge moiety having −n (originating from one or more negatively charged functional groups, which may be the same or different) net charge, wherein n is an integer which may be equal to 1, 2, 3, 4, 5 or 6.

As used herein, a "positively charged moiety of a salt adduct" of the invention is the corresponding acid of pyridoxine, or any derivative thereof. In certain embodiments, the positive charge of the positively charged moiety stems from the protonated basic nitrogen atom of pyridoxine (as for example in compound (2)) or any derivative thereof (such as for example compounds of formula (I)). In certain embodiments, the positively charged pyridoxine derivative is substituted with a positively charged functional group such as for example —$NH_3^+$, —$CH_2NH_3^+$, —$NH_2R^+$, —$NHR_2^+$ (wherein each R is independently a $C_1$-$C_6$ alkyl), which may, in some embodiments, be present in addition to the positively charged protonated basic aromatic nitrogen atom in the pyridine ring.

As used herein, a "carboxylated 5- to 7-membered lactam ring" of a salt adduct of the invention, is meant to encompass a γ-lactam, δ-lactam or ε-lactam rings, having a negatively charged carboxylate group (—$COO^-$) substituted thereto. In certain embodiments, said carboxylate group is substituted at the lactam ring carbon atom adjacent to the amide nitrogen. In another embodiment said carboxylated lactam ring is a L-2-pyrrolidone-5-carboxylate (compound (1)). In other embodiments said carboxylate group is substituted on any position of the lactam ring. In certain embodiments, said carboxylated 5- to 7-membered lactam ring may be substituted by another substituent at any position on the lactam ring.

It should be understood that the present invention encompasses a salt adduct as described herein above and below, provided that when said carboxylated lactam ring is an L-2-pyroglutamate, i.e. compound (1), said positively charged moiety is other than pyridoxine, i.e. compound (2).

In some embodiments of the present invention, said positively charged moiety of a salt adduct of the invention, is a compound of formula (I):

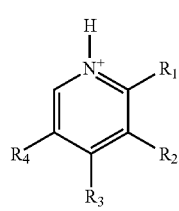

(I)

wherein
$R_1$ is straight or branched $C_1$-$C_6$ alkyl;
$R_2$ is selected from —OH, straight or branched $C_1$-$C_6$ alkoxy, and straight or branched $C_1$-$C_6$ alkoxycarbonyl;
$R_3$ and $R_4$ are each independently selected from a formyl group, straight or branched $C_1$-$C_6$ alkyl optionally substituted by at least one halogen, amine, hydroxyl, $C_1$-$C_6$ alkoxy, thiol, $C_1$-$C_6$ alkoxycarbonyl.

In certain embodiments, said carboxylated lactam ring of a salt adduct of the invention is selected from the group consisting of:

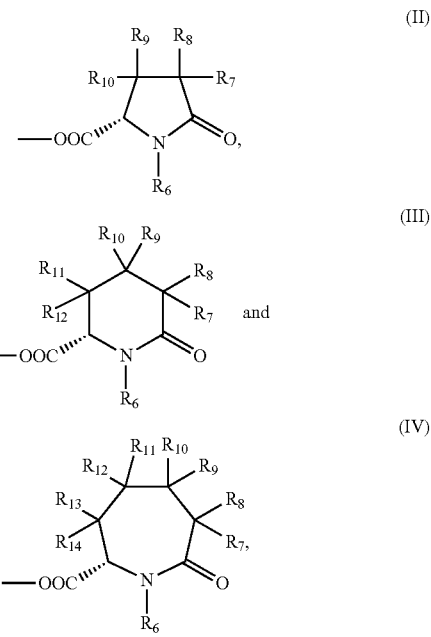

wherein
$R_6$ is selected from H, straight or branched $C_1$-$C_6$ alkyl optionally substituted by one or more halogen atoms, straight or branched $C_2$-$C_6$ alkenyl, straight or branched $C_2$-$C_6$ alkynyl, cycloalkyl, aryl and heteroaryl optionally substituted by $C_1$-$C_6$ alkyl;
$R_7$, $R_8$, $R_9$, $R_{10}$, $R_{11}$, $R_{12}$, $R_{13}$ and $R_{14}$ are each independently selected from H, straight or branched $C_1$-$C_6$ alkyl, $C_2$-$C_6$ alkenyl, $C_2$-$C_6$ alkynyl, cycloalkyl, aryl and heteroaryl optionally substituted by at least one group selected from $C_1$-$C_6$ alkyl, halogen, amino, cyano, nitro, thiol, $C_1$-$C_6$ alkoxy, aminocarbonyl, $C_1$-$C_6$ alkoxycarbonyl, $C_1$-$C_6$ carboxyalkyl, $C_1$-$C_6$ alkoxycarbonylalkyl and amidino.

In certain embodiments, said carboxylated lactam ring is a compound of formula (II):

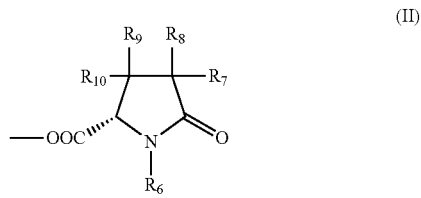

wherein $R_6$, $R_7$, $R_8$, $R_9$ and $R_{10}$ are as defined above. In certain embodiments, $R_6$ is $C_1$-$C_6$ alkyl. In yet further embodiments, $R_9$ is $C_1$-$C_6$ alkyl.

In certain embodiments, said carboxylated lactam ring of a salt adduct is a compound of formula (II):

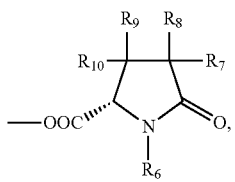

(II)

and said positively charged moiety of a salt adduct is compound (2):

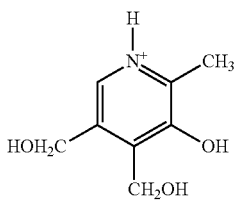

(2)

wherein $R_6$, $R_7$, $R_8$, $R_9$ and $R_{10}$ are as defined above.

In certain embodiments, said carboxylated lactam ring of a salt adduct is compound (1):

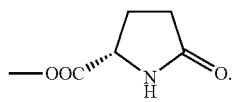

(1)

and said positively charged moiety of a salt adduct is a compound of formula (I):

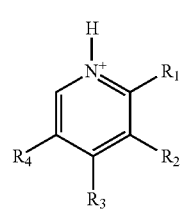

(I)

wherein $R_1$, $R_2$, $R_3$ and $R_4$ are as defined above.

In some embodiments of the above defined salt adduct of the carboxylated lactam ring formula (1) and positively charged compound of formula (I), $R_1$ is a $C_1$-$C_6$ alkyl and $R_2$, $R_3$ and $R_4$ are as defined above. In other embodiments of the above defined salt adduct of the carboxylated lactam ring formula (1) and positively charged compound of formula (I), $R_2$ is selected from hydroxyl and $C_1$-$C_6$ alkoxy; and $R_1$, $R_3$ and $R_4$ are as defined above. In further embodiments of the above defined salt adduct of the carboxylated lactam ring formula (1) and positively charged compound of formula (I), $R_3$ is —$CH_2R_{15}$, wherein $R_{15}$ is selected from —$C_1$-$C_6$ alkoxy, —OH and —$NH_3^+$; and $R_1$, $R_2$ and $R_4$ are as defined above. In yet further embodiments of the above defined salt adduct of the carboxylated lactam ring formula (1) and positively charged compound of formula (I), $R_4$ is selected from formyl and —$CH_2R_{16}$, wherein $R_{16}$ is selected from —$C_1$-$C_6$ alkoxy and —OH; and $R_1$, $R_2$ and $R_3$ are as defined above.

In other embodiments of a salt adduct of the invention, said carboxylated lactam ring is a compound of formula (III):

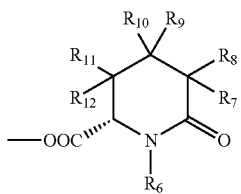

(III)

and said positively charged moiety is a compound of formula (I):

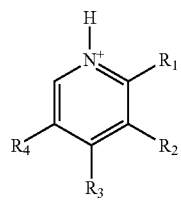

(I)

wherein $R_1$, $R_2$, $R_3$, $R_4$, $R_6$, $R_7$, $R_8$, $R_9$ $R_{10}$, $R_{11}$ and $R_{12}$ are as defined above.

On other embodiments of a salt adduct of the invention, said carboxylated lactam ring is a compound of formula (IV):

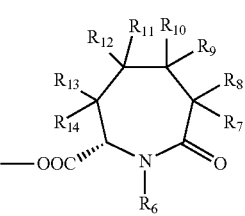

(IV)

and said positively charged moiety is a compound of formula (I):

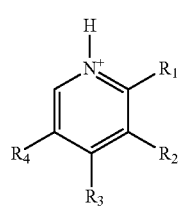

(I)

wherein $R_1$, $R_2$, $R_3$, $R_4$, $R_6$, $R_7$, $R_8$, $R_9$ $R_{10}$, $R_{11}$, $R_{12}$, $R_{13}$ and $R_{14}$ are as defined above.

In one embodiment of the above defined salt adducts said positively charged moiety is a compound of formula (2):

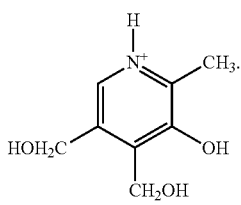

In certain embodiments, the salt adduct is selected from:

1)

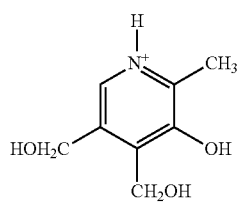

2)

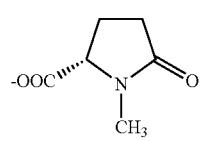

3)

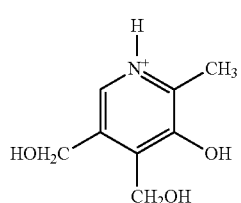

4)

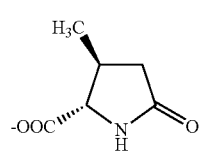

5)

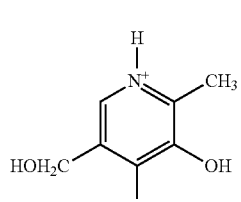

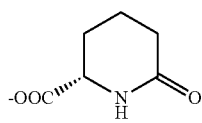

6)

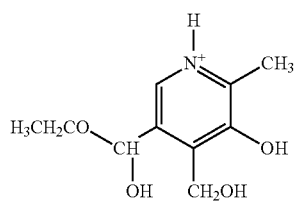

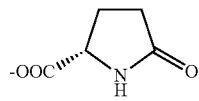

7)

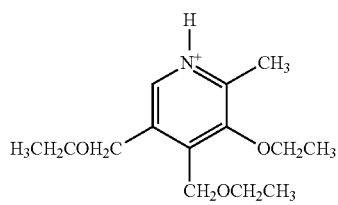

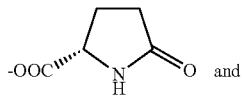 and

8)

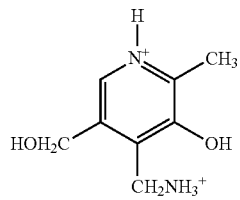

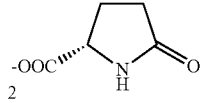

(two pyroglutamate moieties).

The term "halogen" as used herein means F, Cl, Br or I.

The term "$C_1$-$C_6$ alkyl" as used herein represents a saturated, branched or straight hydrocarbon chain having 1, 2, 3, 4, 5 or 6 carbon atoms. Typical $C_{1-6}$ alkyl groups include, but are not limited to, methyl, ethyl, n-propyl, isopropyl, butyl, isobutyl, sec-butyl, tert-butyl, pentyl, isopentyl, hexyl, isohexyl and the like.

The term "$C_2$-$C_6$ alkenyl" as used herein represents a branched or straight hydrocarbon chain having 2, 3, 4, 5 or 6 carbon atoms and at least one double bond positioned between any two carbons of the chain. Examples of such groups include, but are not limited to, ethenyl, 1-propenyl, 2-propenyl, isopropenyl, 1,3-butadienyl, 1-butenyl, 2-butenyl, 1-pentenyl, 2-pentenyl, 1-hexenyl, 2-hexenyl and the like.

The term "$C_2$-$C_6$ alkynyl" as used herein represents a branched or straight hydrocarbon chain having 2, 3, 4, 5 or 6 carbon atoms and at least one triple bond positioned between any two carbons of the chain. Examples of such groups include, but are not limited to, ethynyl, 1-propynyl, 2-propynyl, 1-butynyl, 2-butynyl, 1-pentynyl, 2-pentynyl, 1-hexynyl, 2-hexynyl and the like.

The term "$C_1$-$C_6$ alkoxy" as used herein refers to the radical —O—$C_{1-6}$ alkyl, wherein $C_{1-6}$ alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_1$-$C_6$ alkylthio" as used herein refers to the radical —S—$C_{1-6}$ alkyl, wherein $C_{1-6}$ alkyl is as defined above. Representative examples are methylthio, ethylthio, isopropylthio, n-propylthio, butylthio, pentylthio and the like.

The term "cycloalkyl" as used herein represents a monocyclic, carbocyclic group having 3, 4, 5, 6, 7 or 8 carbon atoms, but may also include heteroatoms such as N, O and/or S. Representative examples are cyclopropyl, cyclobutyl, cyclopentyl, cyclohexyl, cycloheptyl, cyclooctyl and the like.

The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "heteroaryl" as used herein refers to ring systems in which at least one ring is an aromatic ring in which at least one atom is a non-carbon atom, either substituted or non-substituted, where the non-carbon atom may be, for example, a nitrogen, sulfur or oxygen atom.

The term "$C_1$-$C_6$ alkoxycarbonyl" as used herein refers to the radical —C(O)O—$C_{1-6}$ alkyl, wherein $C_{1-6}$ alkyl is as defined above.

The terms "$C_1$-$C_6$ alkoxy" and "$C_1$-$C_6$ alkylthio" as used herein refers to the radicals $C_{1-6}$—O— and $C_{1-6}$—S—, respectively, wherein $C_{1-6}$ alkyl is as defined above.

The term "hydroxyl" as used herein refers to the radical —OH. As used herein the term "thiol" refers to the radical —SH. As used herein the term "formyl" refers to the radical —COH. As used herein the term "cyano" refers to the radical —CN. As used herein the term "nitro" refers to the radical —$NO_2$.

The term "amine" as used herein refers to —$NH_3$ or any primary (—$NH_2R$), secondary (—$NHR_2$), tertiary (—$NR_3$) or quarternary amines (—$NR_4^+$), wherein each R may be the same or different and independently selected from H, $C_1$-$C_6$ alkyl, $C_1$-$C_6$ alkenyl, $C_1$-$C_6$ alkynyl as defined herein above.

The term "$C_1$-$C_6$ carboxyalkyl" as used herein refers to the radical —CO—($C_1$-$C_6$ alkyl), wherein $C_{1-6}$ alkyl is as defined above.

The term "aminocarbonyl" as used herein refers to the radical —$CONR_2$, wherein each of groups R is independently selected from H, $C_1$-$C_6$ alkyl, $C_1$-$C_6$ alkenyl, $C_1$-$C_6$ alkynyl as defined herein above.

The term "alkoxycarbonylalkyl" as used herein refers to the radical —OCO—($C_1$-$C_6$alkyl), wherein $C_{1-6}$ alkyl is as defined above.

The term "amidino" as used herein refers to the radical —C(=NH)—$NH_2$.

The term "optionally substituted" as used herein means that the moieties referred to are either unsubstituted or substituted with one or more of the substituents specified. When the moieties referred to are substituted with more than one substituent the substituents may be the same or different.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

It should be understood that moieties of a salt adduct of the invention may contain each at least one chiral center, and thus may exist in, and be isolated as, any stereoisomer thereof including, enantiomers, diastereomers or any mixtures thereof including, but not limited to racemic mixtures. The present invention includes any possible stereoisomer (e.g. enantiomers, diastereomers), any mixtures thereof including, but not limited to, racemic mixtures, of any of the individual moieties of a salt adduct of the invention. Where the herein-described processes for the preparation of each of the moieties of a salt adduct of the invention give rise to mixtures of stereoisomers, these isomers may be separated by conventional techniques, such as preparative chromatography. The moieties of a salt adduct of the invention may be each prepared in any mixture of possible stereoisomers thereof, including but not limited to racemic mixtures thereof, or individual stereoisomers (e.g. enantiomers, diastereomers) may be prepared either by enantiospecific synthesis or by chiral chromatographic separation of a racemate. Whenever referring to amino acids, the invention should be understood to encompass natural and non-natural amino acids or any derivative thereof.

The term "non-natural amino acid" as used herein refers herein to amino acids, or any derivative thereof, that are not among the amino acids which are the building blocks of proteins having L as well as D-configurations, while "natural amino acids", refer to amino acids or any derivative thereof, which are the building blocks of proteins, having L as well as D-configurations.

Carboxylated 5- to 7-membered lactam rings, which may be optionally substituted as defined hereinabove, may be synthetically prepared by any method known to a person skilled in the art or by methods described herein. In certain embodiments, said carboxylated lactam may be prepared from the corresponding amino acids, such as by methods described herein.

In one aspect, the invention provides methods of preparing, e.g., carboxylated lactam ring of formula (II) (e.g. wherein n=1 for a reactant of formula (IVa) in Scheme 1), carboxylated lactam ring (III) (e.g. wherein n=2 for a reactant of formula (IVa) in Scheme 1) and carboxylated lactam ring of formula (IV) (e.g. wherein n=3 for a reactant of formula (IVa) in Scheme 1), starting from an amino dioic acid of formula (IVa), as depicted in examplery Scheme 1. It should be noted that the amino dioic acid of formula (IVa) may be in the (R) or (S) configuration or any mixture thereof, such as for example the equimolar racemic mixture.

Scheme 1

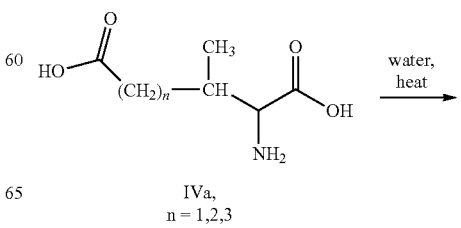

IVa,
n = 1,2,3

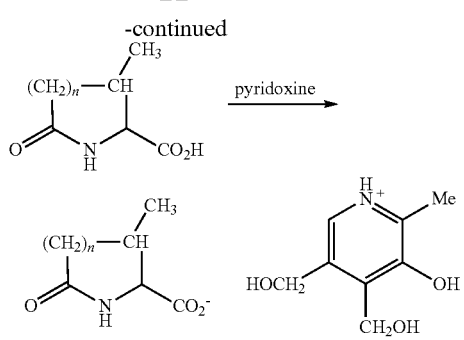

In another aspect, the invention provides methods of synthetically preparing, e.g., carboxylated lactam ring of formula (II) (e.g. wherein n=2 for a reactant of formula (IVb) in Scheme 2), carboxylated lactam ring of (III) (e.g. wherein n=3 for a reactant of formula (IVb) in Scheme 2) and carboxylated lactam ring of formula (IV) (e.g. wherein n=4 for a reactant of formula (IVb) in Scheme 2), as depicted in Scheme 2.

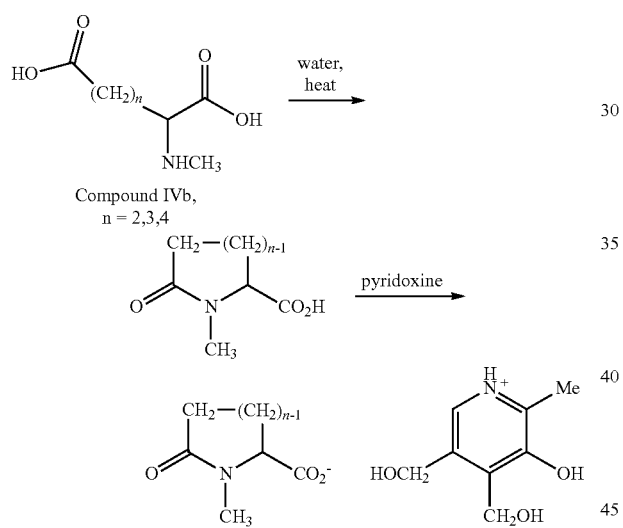

In another aspect, the invention provides methods of preparing a salt adduct including a positively charged pyridoxine moiety, or a derivative thereof, and a carboxylated 5- to 7-membered lactam ring, including the steps of:
(a) suspending an optionally substituted amino dioic acid in water and heating for a sufficient period of time to allow completing lactamization reaction;
(b) optionally decolorizing the reaction mixture to eliminate impurities;
(c) isolating the lactam carboxylate;
(d) optionally purifying the obtained lactam carboxylate by crystallization;
(e) admixing the obtained lactam carboxylate and a pyridoxine base or a derivative thereof in a solvent mixture optionally under heating; and
(f) isolating the product.

In some embodiments of a process of the invention, as described herein above, a decolorizing of step (b) may be carried out by using a decolorizing agent such as activated carbon.

In certain embodiments of a process of the invention, as described herein above, a crystallization of step (d) may be carried out by dissolving the product in an organic solvent and precipitating the purified product by cooling. The solvent used in step (d) may include an alcohol such as, e.g., methanol, ethanol, isopropanol, n-butanol or a ketone such as acetone or methyl ethyl ketone, or a mixture of solvents thereof.

In certain embodiments, a solvent mixture of step (e) includes a mixture of an alcohol such as methanol, ethanol, isopropanol and the like, and water.

According to yet another embodiment, there is provided methods of preparing N-substituted L-pyroglutamic acid and the carboxylate thereof, such as, for example, N-methyl-L-pyroglutamic acid (1-methyl-L-pyroglutamic acid), starting from L-pyroglutamic acid ethyl ester, as depicted in Scheme 3 below.

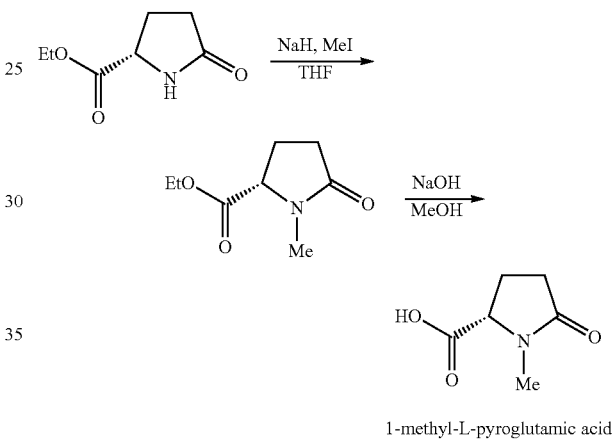

The invention further provides methods of preparing a salt adduct of the invention, wherein said positively charged moiety is a substituted pyridoxine, as depicted in Scheme 4 below. The starting reagent is 2-methyl-3-hydroxy-4-methoxymethyl-5-hydroxymethyl-pyridine hydrochloride (Compound (V)). The preparation of the corresponding salt is described in Example 1.

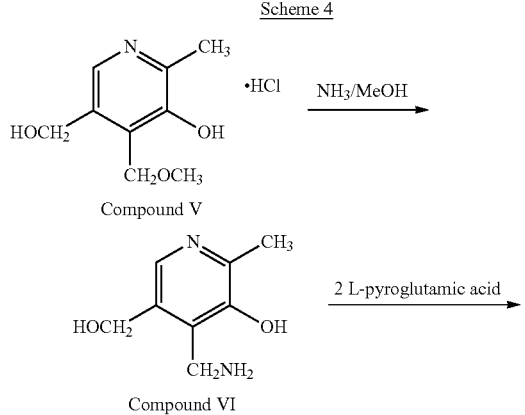

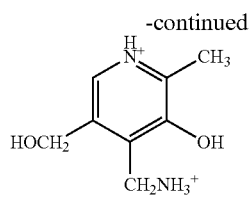

Salt IId

The invention further provides methods of preparing a salt adduct of the invention, wherein said positively charged moiety is a substituted pyridoxine, as depicted in Scheme 5 below. The starting reagent in scheme 5 is 2-methyl-3-hydroxy-4-methoxymethyl-5-hydroxymethyl-pyridine hydrochloride (Compound V). The preparation of the corresponding salt is described in Example 2.

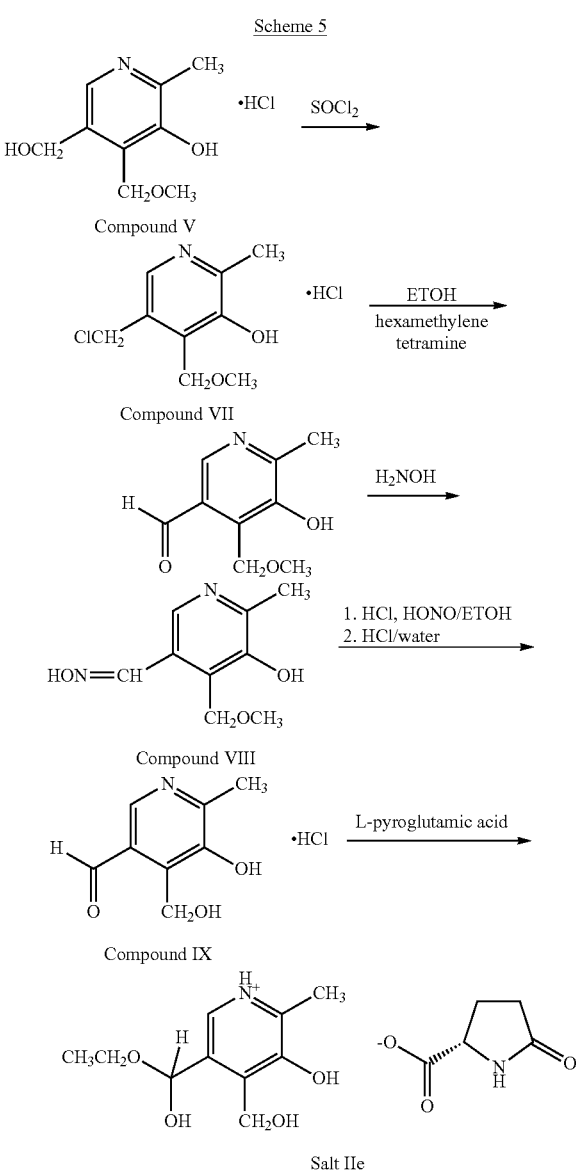

Table 1 depicts several examples of salt adducts of the present invention.

TABLE 1

| Structural formula | Salt No. |
|---|---|
| (pyridoxine derivative with HOCH₂, OH, CH₂NH₃⁺, CH₃ and 2 pyroglutamate) | IId |
| (pyridoxine derivative with CH₃CH₂O, OH, CH₂OH, CH₃ and pyroglutamate) | IIe |
| (pyridoxine derivative with HOCH₂, OH, CH₂OH, Me and piperidinone carboxylate) | IIId |
| (pyridoxine derivative with HOH₂C, OH, CH₂OH, CH₃ and methyl-pyroglutamate) | IIa |
| (pyridoxine derivative with HOCH₂, OH, CH₂OH, Me and N-methyl pyroglutamate) | IIb |
| (pyridoxine derivative with CH₃CH₂OCH₂, OCH₂CH₃, CH₂OCH₂CH₃, Me and pyroglutamate) | IIc |

The salt adducts of the invention may be useful, e.g., for preventing, treating or ameliorating one or more various diseases, conditions or disorders, particularly those associated with or inflicted by alcohol consumption. The expression "associated with" as used herein includes "caused by" or "linked to" or "(usually) occurring together" or "believed to have an impact on" or otherwise linked.

When referring to diseases, conditions or disorders associated with or inflicted by alcohol consumption, it should be understood to encompass any disease, condition or disorder which is associated with any amount or level of alcohol consumption by a subject, including, for example, a minimal amount of alcohol consumption, a moderate amount of alcohol consumption or an excessive amount of alcohol consumption. Additionally, said alcohol consumption may be, for example, sporadic, occasional, continuous, sustained or chronic (or alcohol dependence) over any period of time. In certain embodiments, alcohol consumption by a subject includes, but is not limited to social drinking, session drinking or binge drinking.

Diseases, conditions or disorders associated with or inflicted by alcohol consumption at any of the above amounts or levels, include but are not limited to: alcohol intoxication, alcoholism, cardiovascular disease, hypertension, coronary heart disease, ischemic stroke, nutrient malabsorption, chronic pancreatitis, liver diseases (such as, for example, fatty liver, hepatitis and cirrhosis), cancer, damage to the central nervous system, damage to peripheral nervous system, malignant neoplasms, psychiatric disorders (such as for example major depression, dysthymia, mania, hypomania, panic disorder, phobias, generalized anxiety disorder, personality disorders, schizophrenia, suicide and brain damage).

In another one of its aspects the invention provides a pharmaceutical composition comprising a salt adduct of the invention.

In another aspect of the invention there is provided a pharmaceutical composition comprising a salt adduct of the invention, for use in the treatment or prevention of a disease or disorder associated with or inflicted by alcohol consumption. In some embodiments said pharmaceutical composition comprising a salt adduct of the invention, is intended for use in shortening the half-life of ethanol in the blood of a subject.

In another one of its aspects the invention provides a use of a salt adduct according to the invention, for the preparation of a pharmaceutical composition for the treatment or prevention of a disease or disorder associated with or inflicted by alcohol consumption. In some embodiments, said disease or disorder is selected from alcohol intoxication, alcoholism, cardiovascular disease, hypertension, coronary heart disease, ischemic stroke, nutrient malabsorption, pancreatitis, liver diseases, cancer, CNS damage, neuropsychiatric or neurological impairment, neoplasms and psychiatric disorders or any combination thereof.

In another aspect, the invention provides a use of a salt adduct of the invention, for the preparation of a pharmaceutical composition capable of shortening the half-life of ethanol in the blood of a subject.

When referring to the shortening the half-life of ethanol in the blood of a subject, it should be understood to encompass the ability of a salt adduct of the invention and pharmaceutical compositions comprising it to reduce the time ethanol is cleared from a subject's blood by any amount. The effects of ethanol half-life in the blood may result for example in faster onset of recovery from alcohol intoxication as compared with non-medicated recovery from alcohol intoxication.

The invention further provides a method for treating or preventing a disease or disorder associated with or inflicted by alcohol consumption, comprising administering to a subject in need thereof an effective amount of a salt adduct of the invention. In some embodiments of a method described herein said disease or disorder is selected from alcohol intoxication, alcoholism, cardiovascular disease, hypertension, coronary heart disease, ischemic stroke, nutrient malabsorption, pancreatitis, liver diseases, cancer, CNS damage, neuropsychiatric or neurological impairment, neoplasms and psychiatric disorders or any combination thereof.

In yet a further aspect of the invention, there is provided a method of shortening the half-life of ethanol in the blood of a subject, comprising administering to a subject in need thereof an effective amount of a salt adduct of the invention.

In certain aspects, the invention provides a method for decreasing or preventing symptoms or effects of alcohol consumption in a subject in need thereof. In some embodiment of a method of the invention, said subject has not reached intoxication, and said method comprises administering a composition comprising a salt adduct according to the invention. In certain aspects, the invention provides a method for preventing alcohol intoxication in a subject in need thereof, comprising administering a composition comprising a salt adduct according to the invention. Additional methods of treating a subject are disclosed in PCT Publication No. WO2009004629, incorporated herein by reference.

In any of the various embodiments of the methods of the invention described above, the composition may comprise a salt adduct according to the invention formulated for immediate release, sustained release, controlled release, or a combination of any of the foregoing. In any of the various embodiments of the above described methods, the administration is non-chronic administration. In certain embodiments, a salt adduct according to the invention is formulated for non-chronic administration, and preferably for non-invasive administration. In certain other aspects, the invention provides a method for increasing the mean $t_{max}$ of a salt adduct according to the invention in the blood of a subject in need thereof comprising administering a salt adduct according to the invention formulated for sustained release or controlled release, optionally including a portion of the salt adduct according to the invention formulated for immediate release.

In certain aspects, the invention provides a use of any one of the compositions of the invention in the manufacture of a therapeutic composition useful for practicing each of the methods of the invention as described herein, e.g., for reducing or preventing symptoms or effects of alcohol consumption; for preventing alcohol intoxication; for reducing or eliminating blood alcohol levels in a subject, or for increasing the mean $t_{max}$ of a salt adduct according to the invention in the blood of a subject, among others.

In another aspect of the invention, there is provided a kit for reducing the effect of alcohol intoxication, comprising at least one container comprising a salt adduct of the invention, and instructions for use thereof. In some embodiments, said kit further comprises means for administering said salt adduct.

The present invention also provides delivery devices and kits comprising a salt adduct or composition according to the invention, and methods for their use in the treatment or prevention of alcohol consumption related symptoms. Kits may optionally include means for measuring or monitoring blood alcohol concentration (BAC) levels before, during or after administration of a salt adduct according to the invention.

The term "treatment" as used herein refers to therapeutic treatment. Those in need of treatment are mammalian subjects suffering from any pathologic condition, particularly conditions associated with excessive alcohol consumption or induced by alcohol. By "patient" or "subject in need" is meant any mammal who may be affected by the above-mentioned conditions, and to whom the treatment methods herein described are desired, particularly humans.

Administration of one or more compounds or compositions of the invention to the patient includes both self-administration and administration to the patient by another person.

The active ingredient(s) used by the invention or any composition thereof, may be administered via any mode of administration, for example, buccal, nasal, oral, inhalation, intravenous, intramuscular, subcutaneous, intraperitoneal, parenteral, transmucosal, transdermal, intravaginal, intranasal, mucosal, sublingual, topical, rectal or subcutaneous administration, or any combination thereof. Suitable modes of administration are well known in the art and may be selected by the skilled practitioner in view of the subject and condition to be treated.

The term "therapeutically effective amount" as used herein is intended to mean that amount of a drug or pharmaceutical agent that will elicit the biological or medical response of a tissue, a system, animal or human that is being sought by a researcher, veterinarian, medical doctor or other clinician.

Specific therapeutically effective amounts of the drug administered daily or otherwise by the methods of the invention may range from about 0.005 mg/kg to about 40 mg/kg of body weight, specifically, between about 0.01 to 35 mg/kg, about 0.05 to 30 mg/kg, or about 0.1 to 20 mg/kg. In certain embodiments, the effective amount may be about 1, about 10, about 100, or about 1500 mg, preferably, per day. The effective amount may be about 5 to 1200 mg per day, such as, for example, about 10, about 100, about 500, or about 1000 mg per day. In certain embodiments, the effective amount may be about 1, about 10, about 100, about 200, about 300, about 400, about 500, about 600, about 700, about 800, about 900, about 1000, about 1100, about 1200, about 1300, about 1400, or about 1500 mg, preferably, per day. It should be appreciated that such effective amount may be specific for a human subject. These "human doses" may be calculated by dividing doses (mg/kg) in mice by, for example, about 12 to derive respective Human Equivalent Doses (HED) (mg/kg), and further divided by, for example, 10 (Safety Factor in extrapolating from mice to human), in accordance with the Guidance for Industry, Estimating the Maximum Safe Starting Dose in Initial Clinical Trials for Therapeutics in Adult Healthy Volunteers. [Food and Drug Administration (FDA) and Center for Drug Evaluation and Research (CDER), July (2005)]. The effective amount of the drug is preferably comprised within a dosage unit form. Additionally, the administration of the drugs according to the invention may be periodical, for example, the periodic administration may be effective twice daily, three times daily or at least once daily for at least about, for example, two days, three days, four days, five days, six day, seven days or more to one month, two months, three months, four months, or more. There may be advantages of lower doses, evident to those of skill in the art, that may include, for example, inter alia, a lower risk of side effects, especially in long-term use, and a lower risk of the patients' becoming desensitized to the treatment.

In certain embodiments, unit dosage forms used according to invention may be either for a single or for repeated administration. Administration of said dosage unit form may be repeated, for example, about every one to about five, about ten or about twenty four hours, e.g., for a therapeutically sufficient period of time. In certain embodiment, the unit dosage form may be a sustained-released dosage unit form which provides continued pH-independent drug release for a considerable period of time after administration, e.g., 30 minutes, 1 hour, 2 hours, 3 hours, 4 hours, 5 hours, 6 hours, 7 hours, 8 hours, 9 hours, 10 hours, 11 hours, or 12 hours or more.

The skilled medical practitioner will appreciate that the treatment of different conditions may necessitate the use of different doses and/or different dosage regiments.

Therapeutic formulations may be administered in any conventional dosage formulation. Formulations typically comprise at least one active ingredient, as defined herein, together with one or more acceptable carriers thereof.

The compositions of the invention may comprise a buffering agent, an agent which adjusts the osmolarity thereof, and optionally, one or more pharmaceutically acceptable carriers, excipients and/or additives as known in the art. Supplementary active ingredients may also be incorporated into the compositions. The carrier may be solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating, such as lecithin, by the maintenance of the required particle size in the case of dispersion and by the use of surfactants.

As used herein "pharmaceutically acceptable carrier" may include any solvent, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

Compounds or compositions of the invention (including pharmaceutical compositions, "drugs") may be administered orally. The active compounds or compositions of the invention employed in therapy may be administered in various oral forms including, but not limited to, tablets, capsules, pills, lozenges, powders, granules, elixirs, tinctures, suspensions, syrups, and emulsions. The compounds or compositions of the invention may be delivered by any pharmaceutically acceptable route and in any pharmaceutically acceptable dosage form. These include, but are not limited to the use of oral conventional rapid-release, time controlled-release, and delayed-release pharmaceutical dosage forms. The active drug components may be administered in a mixture with suitable pharmaceutical diluents, excipients or carriers (collectively referred to herein as "carrier" materials) suitably selected to with respect to the intended form of administration.

In instances in which the composition for oral administration is in the form of a tablet or capsule, the compounds or compositions of the invention may be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the compounds or compositions of the invention may be combined with non-toxic pharmaceutically acceptable inert carriers such as ethanol, glycerol, water and the like. When desired or required, suitable binders, lubricants, disintegrating agents and coloring and flavoring agents may also be incorporated into the mixture. Stabilizing agents such as antioxidants, propyl gallate, sodium ascorbate, citric acid, calcium metabisulphite, hydroquinone, and 7-hydroxycoumarin may also be added to stabilize the dosage forms. Other suitable compounds may include gelatin, sweeteners, natural and synthetic gums such as acacia, tragacanth, or alginates, carboxymethylcellulose, polyethylene, glycol, waxes and the like.

Alternatively, the compounds or compositions of the invention may be administered in controlled release formulations such as a slow release or a fast release formulation. Such controlled release formulations may be prepared using methods known to those skilled in the art. The method of administration may be determined by the attending physician or other person skilled in the art after an evaluation of the subject's condition and requirements.

For purposes of parenteral administration, solutions in sesame or peanut oil or in aqueous propylene glycol may be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions may be especially suitable for intravenous, intramuscular, subcutaneous and intraperitoneal injection purposes. The sterile aqueous media employed may be readily obtainable by standard techniques known to those skilled in the art. Methods of preparing various pharmaceutical compositions with a certain amount of active ingredient are known, or will be apparent in light of this disclosure, to those skilled in this art.

The invention further provides a method for preventing or reducing the risk of developing a disease, disorder or pathological conditions associated with or inflicted by alcohol consumption. Such method comprises the administration of a prophylactically effective amount of at least one compound of the invention or of any composition comprising the same, to a person at risk of developing any of the said conditions.

The term "prophylactically effective amount" as used herein is intended to mean that amount of a the drug of the invention or a pharmaceutical composition comprising the same, that will prevent or reduce the risk of occurrence or recurrence of the biological or medical event that is sought to be prevented in a tissue, a system, animal or human.

It should be noted that for the methods of treatment and prevention provided in the present invention, the therapeutically effective amount, or dosage, may be dependent on the severity and responsiveness of the disease state to be treated, with the course of treatment lasting from, for example, several days to several months, or until a cure is effected or a diminution of the disease state is achieved. Optimal dosing schedules may be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art may easily estimate repetition rates for dosing based on measured residence times and concentrations of the compounds of the invention or any composition of the invention in body fluids or tissues. Following successful treatment, it may be desirable to have the patient undergo maintenance therapy to prevent the recurrence of the disease state, wherein the combined composition of the invention is administered in maintenance doses, once or more daily.

According to another aspect, the invention relates to the use of a therapeutically effective amount of at least one compound or composition of the invention or any combination or mixture thereof, in the preparation of a medicament for the treatment or prevention of a disorder, disease or condition associated with or inflicted by alcohol consumption, particularly excessive alcohol consumption as described herein.

It should be noted that where the drug is formulated in an enteric coated dosage form, a substantial release of the compound from the dosage form after oral administration to a patient may be delayed until passage of the dosage form through the stomach.

It is to be understood that the invention is not limited to the particular examples, process steps, and materials disclosed herein as such process steps and materials may vary.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising" "having" "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Certain embodiments of this invention are described herein. Variations of certain embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The redwerences in this specification to any prior publication (or information derived thereof), or to any matter which is known, is not, and should not be taken as an acknowledgment or admission or any form of suggestion that that prior publication (or information derived thereof) or known matter forms part of the common general knowledge in the field of endeavour to which this specification relates.

Reference is now made to the following examples, which together with the above description, serve to illustrate the invention but without in any way limiting its scope. The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications may be made without departing from the spirit and intended scope of the invention.

EXAMPLES

Example 1

Preparation of pyridoxamine, L-2-pyrrolidone-5-carboxylate (Salt IId)

Preparation of Pyridoxine Free Base 1.2 g (5 mmol) of pyridoxamine dihydrochloride (Aldrich) was dissolved in 6 mL water in an Erlenmeyer and a solution of 1 g sodium bicarbonate (12 mmol) in 15 mL water was added with liberation of $CO_2$. The solution was cooled to 0° C. to afford crystallization. After some time, the precipitated crystals were collected by filtration, washed with cold water and dried to yield 0.73 g (87%) of the pyridoxamine free base.

Preparation of L-pyroglutamic Acid 20 g of monosodium glutamate (Aldrich) was mixed with 11 mL of HCl 32% and the pH was adjusted to about 2.5 (using HCl). The mixture was heated to above 100° C. in an autoclave for 10 hours. Then the solution was evaporated to dryness to obtain the L-pyroglutamic acid.

Preparation of the Salt 313 mg of L-pyroglutamic acid (2.43 mmol) was dissolved under heating at about 40° C. in about 4 mL ethanol followed by addition of 409 mg (2.43 mmol) of the free pyridoxamine base (as obtained above) to give a clear solution. The solution was left aside for 3 hours at ambient temperature to give a solid mass. In order to enable mixing, additional 2 mL of ethanol was added and the crystals were cooled for half an hour in ice cold water, collected by filtration, washed with cold ethyl alcohol and dried to yield 600 mg of Salt IId in 83% yield.

$^1$H NMR (DMSO-$d_6$), δ ppm: 1.9 (m, 1H), 2.1 (m 2H), 2.3 (m, 1H), 2.4 (s, 3H), 2.5 (s, 1H), 4.1 (m, 1H), 4.9 (s, 2H), 7.8 (s, 1H), 8.2 (s, 1H)

Example 2

Preparation of 3-hydroxy-5-(hydroxymethyl)-2-methylisonicotinealdehyde-mono ethyl acetal, L-2-pyrrolidone-5-carboxylate (Salt IIe)

Preparation of Pyridoxal Free Base 1.016 g (5 mmol) of pyridoxal hydrochloride (Aldrich) was placed in an Erlenmeyer and a solution of 0.456 g sodium bicarbonate (5.4 mmol) in 5 mL water was added. The resulting solution was set aside for some time and crystals precipitated. The thus precipitated crystals were collected by filtration, washed with cold water and dried to afford 0.68 g of the pyridoxal free base (80% yield).

Preparation of the Salt 471 mg (2.8 mmol) of the pyridoxal free base was dissolved in a mixture of 16.5 mL ethanol and 3.5 mL water and heated to about 60° C., followed by addition of 364 mg (2.8 mmol) of L-pyroglutamic acid to give a clear solution. The solution is left aside and several portions of ethanol were added followed by drying of the solution to dryness to yield 930 mg of Salt IIe as hemiacetal in 93% yield.

$^1$H NMR ($D_2O$), δ ppm: 1.3 (t, 3H), 2.1 (m 1H), 2.4 (m, 2H), 2.5 (m, 1H), 2.6 (s, 3H), 3.7 (q, 2H), 4.3 (m, 1H), 4.7 (s, 2H), 6.7 (s, 1H), 8.1 (s, 1H).

Example 3

Preparation of pyridoxine, (S)-oxo-2-piperidine carboxylate (Salt IIId)

169.2 mg of pyridoxine free base (1 mmol) and 143.1 mg of (S)-oxo-2-piperidine carboxylic acid (1 mmol) (Aldrich) were weighed into a vial and mixed with about 0.2 mL of a solution of isopropyl alcohol containing 4.4% water. The mixture was heated in the closed vial to a temperature of about 35° C. The mixture was gradually cooled to room temperature overnight. Then, about 2.5 mL of isopropyl alcohol was added under boiling to give a clear solution, and the solution was left to cool to room temperature. Diethyl ether was added and the mixture was maintained at a temperature of about −18° C. to afford crystallization. The crystals were obtained by filtration, washed with cold isopropyl alcohol and dried to yield 270 mg of Salt IIId in 86% yield.

$^1$H NMR ($D_2O$), δ ppm: 1.1 (m, 2H), 1.7 (m, 1H), 2.0 (m, 1H), 2.3 (t, 2H), 2.5 (s, 3H), 3.9 (m 1H), 4.7 (s, 2H), 4.9 (s, 2H), 8.0 (s, 1H).

Example 4

Preparation of pyridoxine, L-2-pyrrolidone-4-methyl-5-carboxylate (Salt IIa)

Preparation of L-2-pyrrolidone-4-methyl-5-carboxylate 25 g of chemically pure (2S,3S)-3-methyl glutamic acid are suspended in 25 mL of water in an autoclave and heated at 140° C. for 5 hours. The warm solution is decolorized with activated carbon and cooled gradually to room temperature and then to 4° C., during which time a precipitate is formed. The precipitate is isolated by filtration and crystallized from acetone to obtain white crystals.

Preparation of the Salt 14.3 g of L-2-pyrrolidone-4-methyl-5-carboxylate produced as described above and 16.9 g of pyridoxine base are thoroughly sieved and mixed for half an hour. A solution containing 86 mL isopropanol and 4 mL deionized water is added to the mixture and the resulting solution is stirred for half an hour at 35° C. during which time a thick solid is obtained. The thus formed solid is filtered off and vacuum dried at 38° C. for 24 hours. The resulting solid is dissolved in about 60 mL of boiling isopropanol and the mixture is allowed to reach 38° C. to enable crystallization. The thus formed crystals are filtered off and vacuum dried at 38° C. for additional 24 hours to obtain solid Salt IIa.

Example 5

Preparation of pyridoxine, N-methyl-L-2-pyrrolidone-5-carboxylate (Salt IIb)

L-pyroglutamic acid ethyl ester (10 g, 0.07 mole) is dissolved in tetrahydrofuran (100 mL) and cooled to 0° C. Sodium hydride (2 g, in a 60% suspension in oil, 0.084 mole) is added to the mixture, followed by addition of methyl iodide (5.2 mL, 0.084 mole) under constant mixing. The mixture is allowed to warm up to ambient temperature and mixed for an additional hour. The solvent is evaporated under reduced pressure and water is added (10 mL). The aqueous layer is extracted with dichloromethane, which is evaporated to yield the crude 1-methyl-L-pyroglutamic acid ethyl ester.

The obtained crude 1-methyl-L-pyroglutamic acid ethyl ester is dissolved in methanol (100 mL) and a solution of 2N sodium hydroxide (35 mL) is added. The mixture is heated at reflux for 3 hours then cooled and the methanol is evaporated. The resulting aqueous solution is acidified to pH 2 using HCl 1M, washed with dichloromethane and evaporated to yield 1-methyl-L-pyroglutamic acid.

2.86 g of 1-methyl-L-pyroglutamic acid and 3.38 g of pyridoxine base are thoroughly sieved and mixed for half an hour. A solution containing 20 mL isopropanol and 1 mL deionized water is added to mixture and the resulting solution is stirred for half an hour at 35° C. during which time a thick solid is obtained. The thus formed solid is filtered off and vacuum dried at 38° C. for 24 hours. The resulting solid is dissolved in about 60 mL of boiling isopropanol and the mixture is allowed to reach 38° C. to enable crystallization. The thus formed crystals are filtered off and vacuum dried at 38° C. for additional 24 hours to obtain Salt IIb.

Example 5A

Preparation of 1-methyl-L-pyroglutamic acid 25 g of chemically pure N-methyl-L-glutamic acid is suspended in 25 mL of water in a autoclave and heated to 140° C. for 5 hours. The warm solution is decolorized with activated carbon and cooled gradually to room temperature and then to 4° C., during which time a precipitate is formed. The precipitate is isolated by filtration and crystallized from acetone to obtain white crystals.

Example 6

Preparation of 4,5-bis(ethoxymethyl)-3-ethoxy-2-methyl-pyridine, L-2-pyrrolidone-5-carboxylate (Salt IIc)

Equimolar quantities of pyridoxine, ethyl iodide along with sodium hydroxide are admixed in an autoclave together with DMF and heated to 110° C. for 3 hours. The product is recovered, analyzed by HPLC and purified.

Equimolar quantities of the purified product and L-pyroglutamic acid are thoroughly sieved and mixed for half an hour. A solution containing 20 mL isopropanol and 1 mL deionized water is added to mixture and the resulting solution is stirred for half an hour at 35° C. during which time a thick solid is obtained. The thus formed solid is filtered off and vacuum dried at 38° C. for 24 hours. The resulting solid is dissolved in about 60 mL of boiling isopropanol and the mixture is allowed to reach 38° C. to enable crystallization. The thus formed crystals are filtered off and vacuum dried at 38° C. for additional 24 hours to obtain Salt IIc.

Biological Example A

Reduction of GSH Activity in Human Hepatocellular Carcinoma Cell Line

The efficacy of the salt adducts of the invention is tested according to the GSH content assay described by Gutiérrez-Ruiz, M. C. et al. [*Pharmacological Research*, Vol. 44, No. 5, 2001, ibid.]. Human hepatocellular carcinoma cell line HepG2 are grown in monolayer culture at 37° C. in disposable plastic bottles in a humidified atmosphere of 95% air and 5% $CO_2$. Twenty-four hours after seeding, culture media are changed for serum-free media containing ethanol 50 mM and the tested salts and are incubated for 24 h. Cells are washed twice with PBS and gently scraped into 0.5 mL of PBS. An aliquot is taken to determine protein. Standard curves are established using known GSH dilutions. Reduced (GSH) is measured by glutathione reductase and NADPH followed by reduction of the colorimetric reagent 5-50-dithio-bis-(2-nitrobenzoic acid) by GSH.

Biological Example B

Ethanol Clearance in Animals Treated with Salt Adducts of the Invention

The efficacy of the compounds of the invention is tested according to the method described by Calabrese, V. et al. in *Int. J. Tiss. Reac*. XVII (3) 101-108 (1995). Two groups of male Wistar rats weighing 250-300 g are treated with a dose of 2 g/kg body weight of 20% ethanol solution for seven days. One group is treated with the tested salt 1 hour before ethanol administration. The second group serves as a control. At the end of the treatment period, blood samples are removed at different times by cardiac puncture. The blood is centrifuged and plasma samples are analysed for ethanol content by headspace gas-chromatography. Ethanol concentrations are calculated based on a standard curve comparing peak height between standards and tested samples.

The invention claimed is:

1. A salt adduct comprising a positively charged moiety of formula (I):

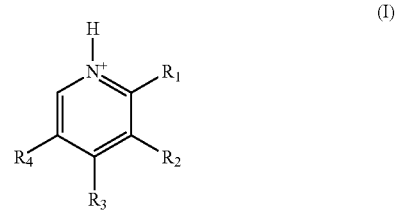

wherein $R_1$ is straight or branched $C_1$-$C_6$ alkyl;

$R_2$ is selected from —OH, straight or branched $C_1$-$C_6$ alkoxy, and straight or branched $C_1$-$C_6$ alkoxycarbonyl;

$R_3$ and $R_4$ are each independently selected from formyl and straight or branched $C_1$-$C_6$ alkyl optionally substituted by at least one halogen, amine, hydroxyl, $C_1$-$C_6$ alkoxy, thiol, or $C_1$-$C_6$ alkoxycarbonyl, and a carboxylated lactam ring is selected from the group consisting of:

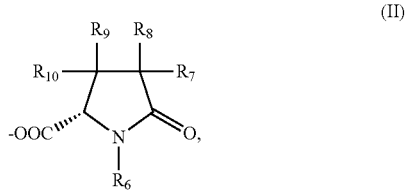

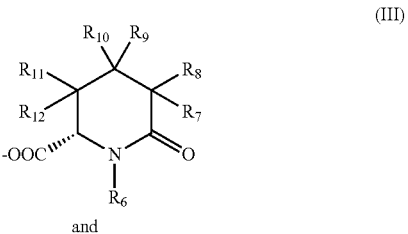

and

-continued (IV)

wherein
- $R_6$ is selected from H, straight or branched $C_1$-$C_6$ alkyl optionally substituted at least one halogen, straight or branched $C_2$-$C_6$ alkenyl, straight or branched $C_2$-$C_6$ alkynyl, cycloalkyl, aryl and heteroaryl optionally substituted by a $C_1$-$C_6$ alkyl;
- $R_7$, $R_8$, $R_9$, $R_{10}$, $R_{11}$, $R_{12}$, $R_{13}$ and $R_{14}$ are each independently selected from H, straight or branched $C_1$-$C_6$ alkyl, $C_2$-$C_6$ alkenyl, $C_2$-$C_6$ alkynyl, cycloalkyl, aryl and heteroaryl optionally substituted by at least one group selected from $C_1$-$C_6$ alkyl, halogen, amino, cyano, nitro, thiol, $C_1$-$C_6$ alkoxy, aminocarbonyl, $C_1$-$C_6$ alkoxycarbonyl, $C_1$-$C_6$ carboxyalkyl, $C_1$-$C_6$ alkoxycarbonylalkyl and amidino, wherein the salt adduct is not metadoxine.

2. The salt adduct according to claim 1, wherein said carboxylated lactam ring is a compound of formula (II):

(II)

and
said positively charged moiety is compound (2):

(2)

- $R_6$ is selected from H, straight or branched $C_1$-$C_6$ alkyl optionally substituted by at least one halogen, straight or branched $C_2$-$C_6$ alkenyl, straight or branched $C_2$-$C_6$ alkynyl, cycloalkyl, aryl and heteroaryl optionally substituted by a $C_1$-$C_6$ alkyl;
- $R_7$, $R_8$, $R_9$, $R_{10}$ are each independently selected from H, straight or branched $C_1$-$C_6$ alkyl, $C_2$-$C_6$ alkenyl, $C_2$-$C_6$ alkynyl, cycloalkyl, aryl and heteroaryl optionally substituted by at least one group selected from $C_1$-$C_6$ alkyl, halogen, amino, cyano, nitro, thiol, $C_1$-$C_6$ alkoxy, aminocarbonyl, $C_1$-$C_6$ alkoxycarbonyl, $C_1$-$C_6$ carboxyalkyl, $C_1$-$C_6$ alkoxycarbonylalkyl and amidino.

3. The salt adduct according to claim 1, wherein said carboxylated lactam ring is compound (1):

(1)

and
said positively charged moiety is a compound of formula (I):

(I)

wherein
- $R_1$ is straight or branched $C_1$-$C_6$ alkyl;
- $R_2$ is selected from —OH, straight or branched $C_1$-$C_6$ alkoxy, and straight or branched $C_1$-$C_6$ alkoxycarbonyl;
- $R_3$ and $R_4$ are each independently selected from formyl and straight or branched $C_1$-$C_6$ alkyl optionally substituted by at least one halogen, amine, hydroxyl, $C_1$-$C_6$ alkoxy, thiol, or $C_1$-$C_6$ alkoxycarbonyl.

4. The salt adduct according to claim 1, wherein said carboxylated lactam ring is compound (1):

(1)

and
said positively charged moiety is a compound of formula (I):

(I)

wherein $R_1$ is a $C_1$-$C_6$ alkyl;
- $R_2$ is selected from —OH, straight or branched $C_1$-$C_6$ alkoxy, and straight or branched $C_1$-$C_6$ alkoxycarbonyl;
- $R_3$ and $R_4$ are each independently selected from formyl and straight or branched $C_1$-$C_6$ alkyl optionally substituted by at least one halogen, amine, hydroxyl, $C_1$-$C_6$ alkoxy, thiol, or $C_1$-$C_6$ alkoxycarbonyl.

5. The salt adduct according to claim 1, wherein said carboxylated lactam ring is compound (1):

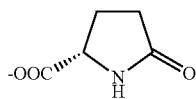

and said positively charged moiety is a compound of formula (I):

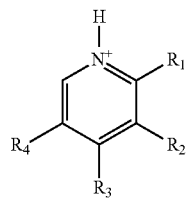

wherein $R_2$ is selected from —OH and $C_1$-$C_6$ alkoxy; and $R_1$ is straight or branched $C_1$-$C_6$ alkyl;

$R_3$ and $R_4$ are each independently selected from formyl and straight or branched $C_1$-$C_6$ alkyl optionally substituted by at least one halogen, amine, hydroxyl, $C_1$-$C_6$ alkoxy, thiol, or $C_1$-$C_6$ alkoxycarbonyl.

6. The salt adduct according to claim 1, wherein said carboxylated lactam ring is compound (1):

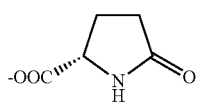

and said positively charged moiety is a compound of formula (I):

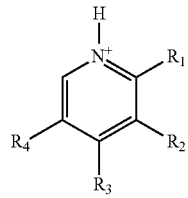

wherein $R_3$ is —$CH_2R_{15}$, wherein $R_{15}$ is selected from —$C_1$-$C_6$ alkoxy, —OH and —$NH_3^+$; and $R_1$ is straight or branched $C_1$-$C_6$ alkyl;

$R_2$ is selected from —OH, straight or branched $C_1$-$C_6$ alkoxy, and straight or branched $C_1$-$C_6$ alkoxycarbonyl;

$R_4$ is selected from formyl and straight or branched $C_1$-$C_6$ alkyl optionally substituted by at least one halogen, amine, hydroxyl, $C_1$-$C_6$ alkoxy, thiol, or $C_1$-$C_6$ alkoxycarbonyl.

7. The salt adduct according to claim 1, wherein said carboxylated lactam ring is compound (1):

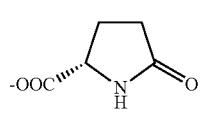

and said positively charged moiety is a compound of formula (I):

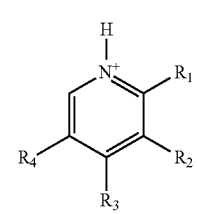

wherein $R_4$ is selected from formyl and —$CH_2R_{16}$, wherein $R_{16}$ is selected from —$C_1$-$C_6$ alkoxy and —OH; and $R_1$ is straight or branched $C_1$-$C_6$ alkyl;

$R_2$ is selected from —OH, straight or branched $C_1$-$C_6$ alkoxy, and straight or branched $C_1$-$C_6$ alkoxycarbonyl;

$R_3$ is selected from formyl, straight or branched $C_1$-$C_6$ alkyl optionally substituted by at least one halogen, amine, hydroxyl, $C_1$-$C_6$ alkoxy, thiol, $C_1$-$C_6$ alkoxycarbonyl.

8. The salt adduct according to claim 1, wherein said carboxylated lactam ring is a compound of formula (II):

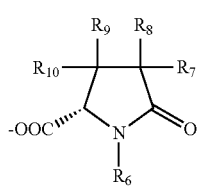

wherein $R_6$ is selected from H, straight or branched $C_1$-$C_6$ alkyl optionally substituted by at least one halogen, straight or branched $C_2$-$C_6$ alkenyl, straight or branched $C_2$-$C_6$ alkynyl, cycloalkyl, aryl and heteroaryl optionally substituted by a $C_1$-$C_6$ alkyl;

$R_7$, $R_8$, $R_9$, $R_{10}$ are each independently selected from H, straight or branched $C_1$-$C_6$ alkyl, $C_2$-$C_6$ alkenyl, $C_2$-$C_6$ alkynyl, cycloalkyl, aryl and heteroaryl optionally substituted by at least one group selected from $C_1$-$C_6$ alkyl, halogen, amino, cyano, nitro, thiol, $C_1$-$C_6$ alkoxy, aminocarbonyl, $C_1$-$C_6$ alkoxycarbonyl, $C_1$-$C_6$ carboxyalkyl, $C_1$-$C_6$ alkoxycarbonylalkyl and amidino.

9. The salt adduct according to claim 1, wherein said carboxylated lactam ring is a compound of formula (II):

(II)

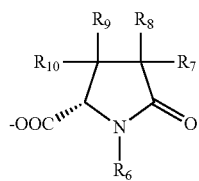

(I)

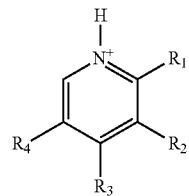

wherein $R_6$ is $C_1$-$C_6$ alkyl and $R_7$, $R_8$, $R_9$, $R_{10}$ are each independently selected from H, straight or branched $C_1$-$C_6$ alkyl, $C_2$-$C_6$ alkenyl, $C_2$-$C_6$ alkynyl, cycloalkyl, aryl and heteroaryl optionally substituted by at least one group selected from $C_1$-$C_6$ alkyl, halogen, amino, cyano, nitro, thiol, $C_1$-$C_6$ alkoxy, aminocarbonyl, $C_1$-$C_6$ alkoxycarbonyl, $C_1$-$C_6$ carboxyalkyl, $C_1$-$C_6$ alkoxycarbonylalkyl and amidino.

10. The salt adduct according to claim 1, wherein said carboxylated lactam ring is a compound of formula (II):

(II)

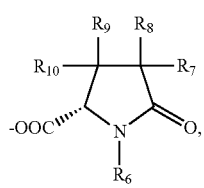

wherein $R_9$ is $C_1$-$C_6$ alkyl, $R_6$ is selected from H, straight or branched $C_1$-$C_6$ alkyl optionally substituted by at least one halogen, straight or branched $C_2$-$C_6$ alkenyl, straight or branched $C_2$-$C_6$ alkynyl, cycloalkyl, aryl and heteroaryl optionally substituted by a $C_1$-$C_6$ alkyl;

$R_7$, $R_8$, $R_9$, $R_{10}$ are each independently selected from H, straight or branched $C_1$-$C_6$ alkyl, $C_2$-$C_6$ alkenyl, $C_2$-$C_6$ alkynyl, cycloalkyl, aryl and heteroaryl optionally substituted by at least one group selected from $C_1$-$C_6$ alkyl, halogen, amino, cyano, nitro, thiol, $C_1$-$C_6$ alkoxy, aminocarbonyl, $C_1$-$C_6$ alkoxycarbonyl, $C_1$-$C_6$ carboxyalkyl, $C_1$-$C_6$ alkoxycarbonylalkyl and amidino.

11. The salt adduct according to claim 1, wherein said carboxylated lactam ring is a compound of formula (III):

(III)

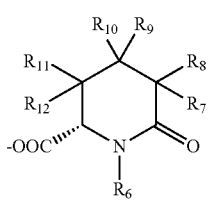

and
said positively charged moiety is a compound of formula (I):

wherein $R_1$ is straight or branched $C_1$-$C_6$ alkyl;

$R_2$ is selected from —OH, straight or branched $C_1$-$C_6$ alkoxy, and straight or branched $C_1$-$C_6$ alkoxycarbonyl;

$R_3$ and $R_4$ are each independently selected from formyl, straight or branched $C_1$-$C_6$ alkyl optionally substituted by at least one halogen, amine, hydroxyl, $C_1$-$C_6$ alkoxy, thiol, $C_1$-$C_6$ alkoxycarbonyl $R_6$ is selected from H, straight or branched $C_1$-$C_6$ alkyl optionally substituted by at least one halogen, straight or branched $C_2$-$C_6$ alkenyl, straight or branched $C_2$-$C_6$ alkynyl, cycloalkyl, aryl and heteroaryl optionally substituted by a $C_1$-$C_6$ alkyl;

$R_7$, $R_8$, $R_9$, $R_{10}$, $R_{11}$, $R_{12}$, $R_{13}$ and $R_{14}$ are each independently selected from H, straight or branched $C_1$-$C_6$ alkyl, $C_2$-$C_6$ alkenyl, $C_2$-$C_6$ alkynyl, cycloalkyl, aryl and heteroaryl optionally substituted by at least one group selected from $C_1$-$C_6$ alkyl, halogen, amino, cyano, nitro, thiol, $C_1$-$C_6$ alkoxy, aminocarbonyl, $C_1$-$C_6$ alkoxycarbonyl, $C_1$-$C_6$ carboxyalkyl, $C_1$-$C_6$ alkoxycarbonylalkyl and amidino.

12. The salt adduct according to claim 1, wherein said carboxylated lactam ring is a compound of formula (IV):

(IV)

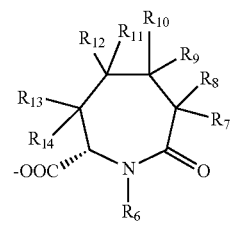

and
said positively charged moiety is a compound of formula (I):

(I)

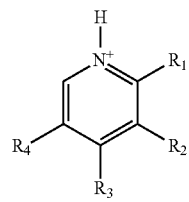

wherein $R_1$ is straight or branched $C_1$-$C_6$ alkyl;

$R_2$ is selected from —OH, straight or branched $C_1$-$C_6$ alkoxy, and straight or branched $C_1$-$C_6$ alkoxycarbonyl;

$R_3$ and $R_4$ are each independently selected from formyl, straight or branched $C_1$-$C_6$ alkyl optionally substituted by at least one halogen, amine, hydroxyl, $C_1$-$C_6$ alkoxy, thiol, $C_1$-$C_6$ alkoxycarbonyl $R_6$ is selected from H, straight or branched $C_1$-$C_6$ alkyl optionally substituted by at least one halogen, straight or branched $C_2$-$C_6$ alkenyl, straight or branched $C_2$-$C_6$ alkynyl, cycloalkyl, aryl and heteroaryl optionally substituted by a $C_1$-$C_6$ alkyl;

$R_7$, $R_8$, $R_9$, $R_{10}$, $R_{11}$, $R_{12}$, $R_{13}$ and $R_{14}$ are each independently selected from H, straight or branched $C_1$-$C_6$ alkyl, $C_2$-$C_6$ alkenyl, $C_2$-$C_6$ alkynyl, cycloalkyl, aryl, and heteroaryl optionally substituted by at least one group selected from $C_1$-$C_6$ alkyl, halogen, amino, cyano, nitro, thiol, $C_1$-$C_6$ alkoxy, aminocarbonyl, $C_1$-$C_6$ alkoxycarbonyl, $C_1$-$C_6$ carboxyalkyl, $C_1$-$C_6$ alkoxycarbonylalkyl and amidino.

13. The salt adduct according to claim 1, selected from the following group:

1)

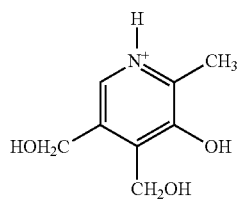
(2)

2)

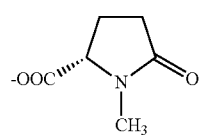
(3)

3)

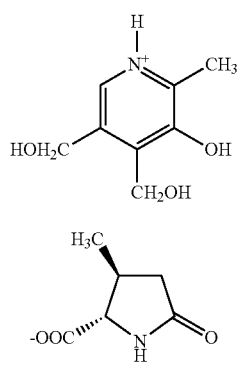
(2)

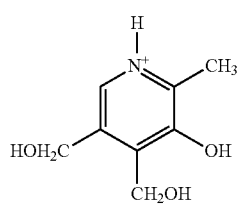
(2)

-continued

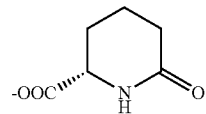
(5)

4)

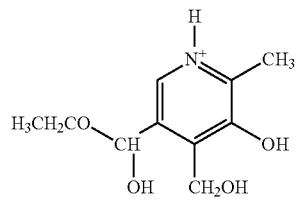
(6)

5)

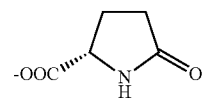
(1)

6)

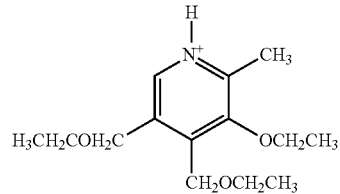
(7)

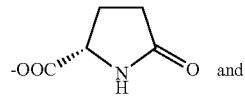
(1) and

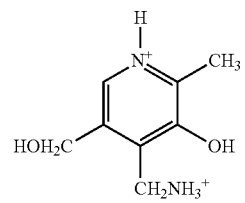
(8)

2· 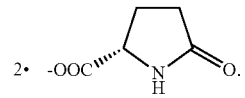
(1)

14. A pharmaceutical composition comprising a salt adduct of claim 1 and a pharmaceutically acceptable carrier.

* * * * *